United States Patent
Broberg

[11] Patent Number: 5,993,211
[45] Date of Patent: Nov. 30, 1999

[54] BALL IMPRESSION COPING

[75] Inventor: Leif Broberg, Göteborg, Sweden

[73] Assignee: Astra Aktiebolag, Sodertalje, Sweden

[21] Appl. No.: 08/647,945

[22] PCT Filed: Apr. 17, 1996

[86] PCT No.: PCT/SE96/00491

§ 371 Date: May 30, 1996

§ 102(e) Date: May 30, 1996

[87] PCT Pub. No.: WO96/34576

PCT Pub. Date: Nov. 7, 1996

[30] Foreign Application Priority Data

May 3, 1995 [SE] Sweden .................................. 95401632

[51] Int. Cl.$^6$ ................................................. A61C 8/00
[52] U.S. Cl. ............................................ 433/172; 433/214
[58] Field of Search .................................. 433/172, 173, 433/174, 214, 213

[56] References Cited

U.S. PATENT DOCUMENTS

| | | |
|---|---|---|
| 4,955,811 | 9/1990 | Lazarra et al. . |
| 5,040,983 | 8/1991 | Binon . |
| 5,071,350 | 12/1991 | Niznick ................ 433/174 X |
| 5,073,110 | 12/1991 | Barbone . |
| 5,194,000 | 3/1993 | Durg ..................... 433/174 X |
| 5,417,570 | 5/1995 | Zuest et al. ........... 433/173 X |
| 5,520,540 | 5/1996 | Nardi et al. .......... 433/173 X |

*Primary Examiner*—Nicholas D. Lucchesi
*Attorney, Agent, or Firm*—White & Case LLP

[57] ABSTRACT

The present invention relates to a temporary ball impression coping (1) for use during the preparation of a overdenture having ball attachment devices for attaching said overdenture to fixtures in the jaw. The coping (1) is provided with a bore (4) for cooperation with a ball part on said ball attachment device. The bore has a cross-section which is polygonal in shape.

6 Claims, 3 Drawing Sheets

BALL IMPRESSION COPING

TECHNICAL FIELD OF THE INVENTION

The present invention relates to ball attachment devices, in particular for overdentures in which posts or abutments carrying a ball part are attached to a fixture in the jawbone and complementary snap fasteners or ball housings are mounted in the overdenture, and more particularly to a temporary coping for use during the preparation of a overdenture having ball attachment devices.

BACKGROUND TO THE INVENTION

The preparation of overdentures involves a series of positive and negative impressions and casts which are used so as to adapt the overdenture to the shape of the oral cavity and so as to orient the fastener elements in the jaw and in the overdenture correctly in relation to each other. During this casting-impression procedure, a temporary coping is placed upon the ball abutments in the jaw and moulded into an impression in an impression spoon. The copings have a bore which is complementary to the ball parts of the ball attachment devices. The copings, which now are located in the impression, are then utilized to hold ball abutment replicas which are moulded into a positive model of the jaw cast into the impression. The snap fasteners or ball housings are then attached to the temporary ball abutment replicas and moulded into or otherwise attached to the overdenture.

The copings normally have an interior bore which is circular in cross-section. This means that the fit between the coping and the ball part has to be very exact. If the bore is too small, it will be difficult to press the coping onto the ball part, and if the bore is too wide, there will be no or insufficient friction to hold the ball abutment and the abutment replica securely. Furthermore, special arrangements have to be made in order to allow the air in the bore to escape, such as channels to the outside etc.

It thus is desirable that there is a specified friction between the bore in the coping and the ball parts of the respective ball abutment This sets a high standard in regard of the dimensional precision of the bore. It furthermore is desirable that any air present in the interior of the coping has a possibility of escaping when the coping is pushed down onto the ball part in order to allow the coping to be fully seated on the ball part.

DISCLOSURE OF THE INVENTION

We have now found that the above disadvantages with known copings may be overcome by using a ball impression ball coping in which the interior bore has a cross-section which is polygonal in shape.

Thus, according to the present invention there is provided a temporary ball impression coping for use during the preparation of a overdenture having ball attachment devices for attaching said overdenture to fixtures in the jaw, said coping being provided with a bore for cooperation with a ball part on said ball attachment device, characterized in that said bore has a cross-section which is polygonal in shape.

Such a ball impression coping can overcome the disadvantages inherent in the prior art whilst still being simple and inexpensive to manufacture.

The bore may be any type of polygon. However, preferably the bore has a polygonal cross-section which is regular. In a further preferred embodiment, the polygonal shape is hexagonal.

The sides of said polygonal shape may be curved inwardly. The sides of the polygonal cross-section may also be formed of two parts having the same length and being angled inwardly in relation to each other so as to form a star shape.

Preferably the mouth of the bore is provided with a conically flaring part for cooperation with a corresponding conical part on said ball attachment abutment.

BRIEF DESCRIPTION OF THE DRAWINGS

A preferred embodiment of the invention will now be described, by way of example, with reference to the attached drawings in which.

DETAILED DESCRIPTION OF A PREFERRED EMBODIMENT OF THE INVENTION

Figure 1:
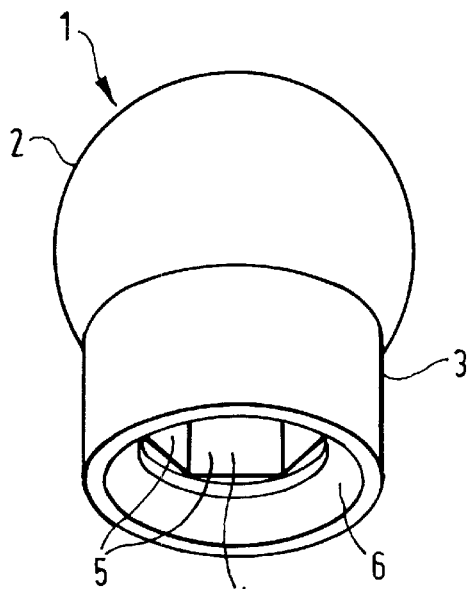
FIG. 1 is a perspective view of a impression coping according to the invention.
Figure 2:
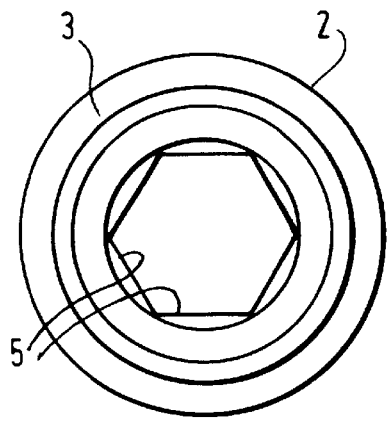
FIG. 2 is a plan view of the coping in FIG. 1, and FIGS. 3–10 illustrate the use of the ball impression coping.

As can be seen in FIGS. 1 and 2, a ball impression coping 1 according to the invention is provided with a spherical top portion 2 intended to be moulded into the impression and a lower cylindrical part 3 (upper and lower referring to the orientation of the coping in FIG. 1). A central bore 4 extends from the lower end of the cylindrical part 3. The inner side of the bore 4 has walls 5 providing the cross-section of the bore 4 with a regular hexagonal shape. The outer part of the bore 4 is provided with a conically flaring part 6 intended to fit snugly against a corresponding part 8 on a ball abutment 7 or a ball abutment replica (see FIG. 3). The dimensions of the hexagon are such so as to circumscribe a circle having a diameter slightly smaller than the diameter of the major circular cross-section of the ball-shaped part 9 of the ball abutment 7 so as to provide a slight press fit when the ball impression coping 1 is pushed down onto the ball part of the ball abutment.

The ball impression coping is made of a suitable resilient plastics material, such as polypropylene.

The two complementary conically shaped parts 6 and 8 will ensure that the coping and the ball abutment will be exactly and reproducibly oriented relative to each other when the two parts are fitted together.

One result of the hexagonal shape of the bore in the coping is that the engagement between the inside of the bore and the ball part will only be along the centre lines of the respective inside wall of the bore, which has some important advantages. The friction between the two parts will be well defined and relatively easy to determine in advance by defining the relative sizes of the two parts. The attainment of a predetermined minimum friction is also facilitated A further advantage of the hexagonal (polygonal) shape of the bore is that the air contained in the bore easily can escape past the ball-shaped part through the channels formed at the corners of the hexagonal bore, thus allowing the conical parts on the coping and on the ball abutment to fully engage each other. The location of the channels lessens the risk that any impression material may penetrate into the bore, endangering the desired fit between coping and ball abutment.

Figure 3:
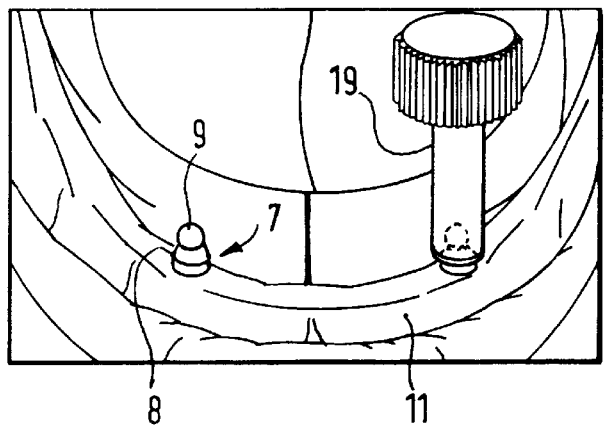
Figure 4:
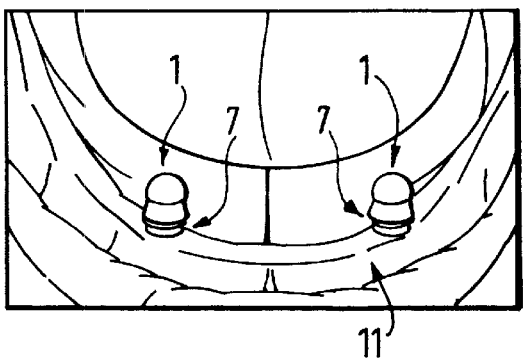
Figure 5:
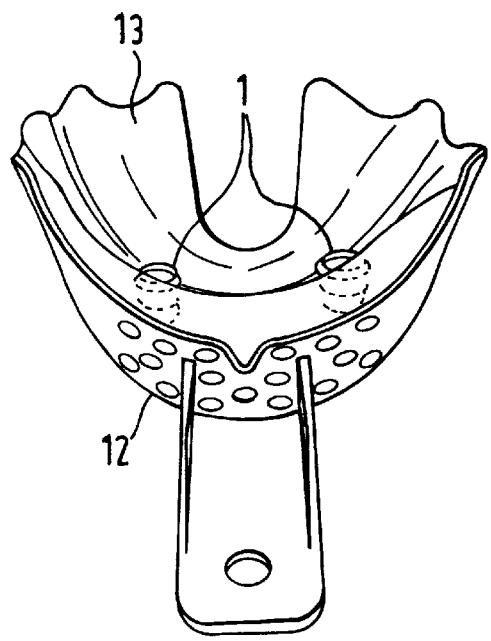
Figure 6:
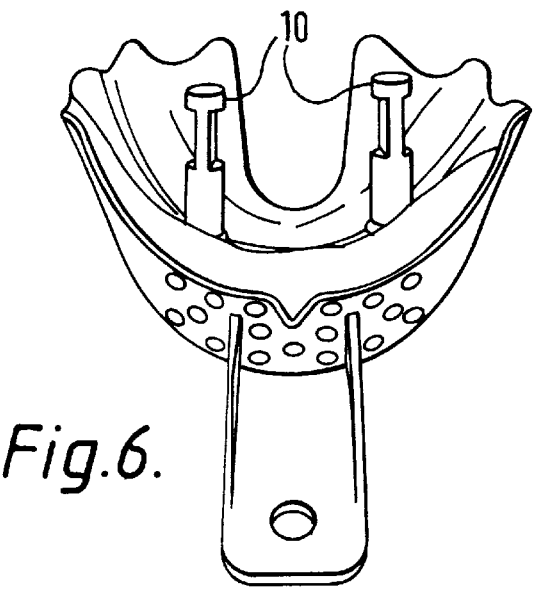
Figure 7:
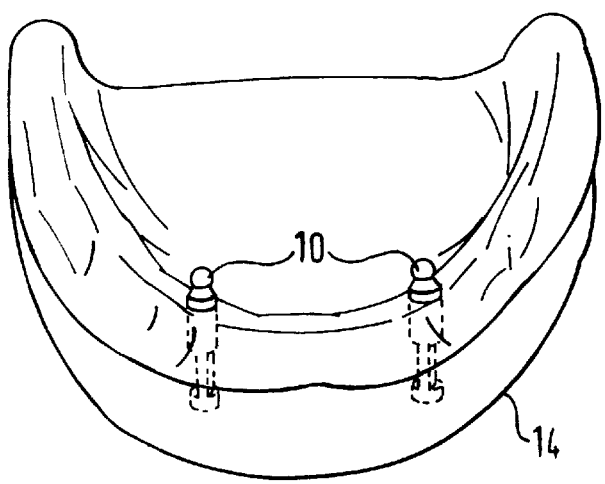

The use of the coping is illustrated in FIGS. 3–10. FIG. 3 shows how the ball abutments 7 are mounted on the fixtures in the jaw 11 by means of a suitable instrument 19. As an be seen in FIG. 4, the ball impression copings I are then pressed down onto the ball abutments 7 so as to bring the respective conical parts thereof 6, 8 into full engagement, thus ensuring a distinct and definite orientation between the two parts. An impression tray 12 containing impression material 13 is then pressed down over the impression copings 1 and the impression material is allowed to harden, forming a negative model. The impression tray 12 is then removed, still holding the impression material 13, and, as can be seen in FIG. 5, the impression copings are held in the hardened impression material. Ball abutment replicas 10 (see FIG. 7) are then mounted in the copings 1 in the impression material. A positive model 14 of the jaw is then cast with aid of the negative impression model. The abutment replicas 10 will thus be moulded into and held in the positive jaw model.

The regularity of the polygonal cross-section of the bore will entail that the ball-shaped part of the abutments 7 and the abutment replicas will be centred in the coping. The abutment replicas 10 will be oriented in the same way in the positive jaw model 14 as the ball abutments 7 mounted on the fixtures in the jaw bone 11 (see FIG. 7).

Figure 8:
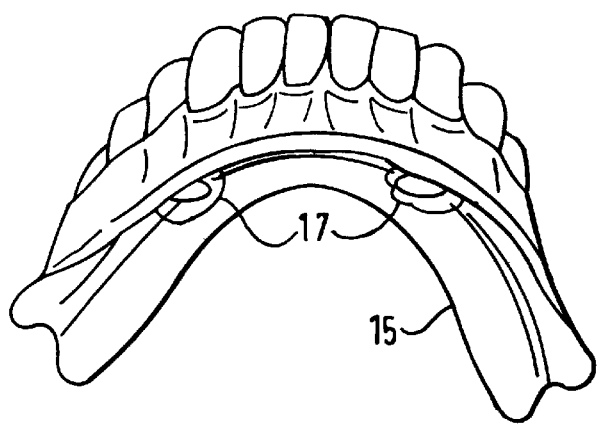
Figure 9:
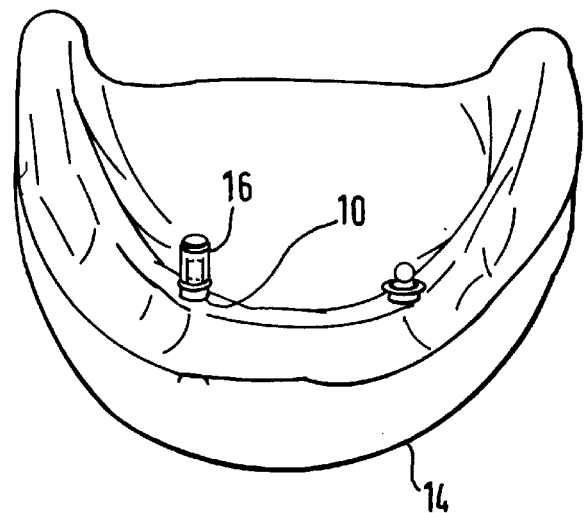
Figure 10A:
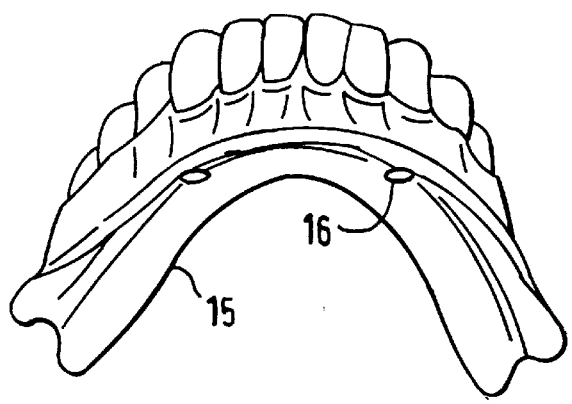
Figure 10B:
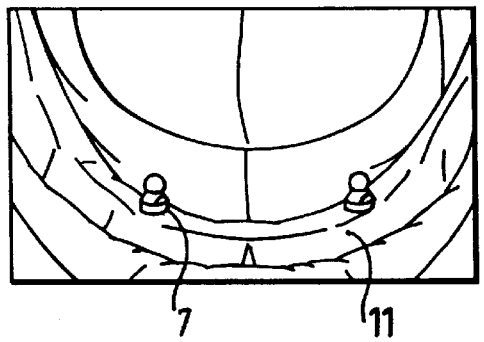

The ball housings 16 are then mounted on the ball abutment replicas 10, see FIG. 9, and the overdenture 15 is relieved or provided with bores 17 in the locations corresponding to the ball housings 16, see FIG. 8. The bores 17 in the overdenture are then at least party filled with a hardening material and the overdenture 15 is fitted onto the jaw model 14 and the ball housings 16. When the material in the bores 17 of the overdenture 15 has set, fixing the ball housings 16 securely, the overdenture 15 can be removed from the abutment replicas 10 and the overdenture is now ready for use, see FIGS. 10a and 10b.

The overdenture need of course not be an existing overdenture. The denture may also be prepared during the procedure described above with the aid of the positive model of the jaw.

The invention may of course be varied in many ways within the scope of the appended claims. For instance, in the above preferred embodiment the cross-section of the bore has been described as having a hexagonal shape. Any regular polygonal shape is however possible, for instance regular polygons having three, four, five, seven or eight sides. The walls of the polygons may also be curved inwardly from the corners of the polygon or even be formed by two parts oriented at an angle relative to each other, thus giving the cross-section a star-shaped form, for instance a double-hex shape.

The coping further has been described as having a spherical part which is to be moulded into the impression material. This part of the coping may however have any shape which provides a reasonably good retention in the hardened impression material.

I claim:

1. A temporary ball impression coping for use during the preparation of an overdenture having a ball attachment device for attaching said overdenture to a ball part of an anchoring structure anchored to a jaw bone of a toothless patient, said coping being provided with a bore for co-operation with the ball part, characterized in that said bore has a cross-section which is polygonal in shape.

2. A coping according to claim 1, characterized in that said bore has a polygonal cross-section which is regular.

3. A coping according to claim 1 or 2, characterized in that said polygonal shape is hexagonal.

4. A coping according to claim 1 or 2, characterized in that the sides of said polygonal shape are curved inwardly.

5. A coping according to claim 1 or 2, characterized in that the sides of said polygonal cross-section are formed of two parts having essentially the same length and being angled inwardly in relation to each other so as to form a star shape.

6. A coping according to claim 1 or 2, characterized in that the mouth of said bore is provided with a conically flaring part for co-operation with a corresponding conical part on said ball part.

* * * * *